US011253674B2

United States Patent
Le Van Quyen et al.

(10) Patent No.: US 11,253,674 B2
(45) Date of Patent: Feb. 22, 2022

(54) SYSTEM FOR BILATERAL IN-EAR EEG RECORDING WITH CLOSED-LOOP BINAURAL SENSORY STIMULATION

(71) Applicants: ICM (INSTITUT DU CERVEAU ET DE LA MOELLE ÉPINIÈRE), Paris (FR); APHP (ASSISTANCE PUBLIQUE—HÔPITAUX DE PARIS), Paris (FR); CENTRE NATIONAL DE LA RECHERCHE SCIENTIFIQUE, Paris (FR); SORBONNE UNIVERSITE, Paris (FR); INSERM (INSTITUT NATIONAL DE LA SANTÉ ET DE LA RECHERCHE MÉDICALE), Paris (FR)

(72) Inventors: Michel Le Van Quyen, Paris (FR); Alexis Genin, Saint leu d'Esserent (FR); Alexis Steiner, Dijon (FR); Mario Valderrama, Bogotá (CO); Miguel Navarrete, Bogotá (CO)

(73) Assignees: ICM (INSTITUT DU CERVEAU ET DE LA MOELLE ÉPINIÈRE), Paris (FR); APHP (ASSISTANCE PUBLIQUE—HÔPITAUX DE PARIS), Paris (FR); CENTRE NATIONAL DE LA RECHERCHE SCIENTIFIQUE (CNRS), Paris (FR); SORBONNE UNIVERSITE, Paris (FR); INSERM (INSTITUT NATIONAL DE LA SANTÉ ET DE LA RECHERCHE MEDICALE), Paris (FR)

( * ) Notice: Subject to any disclaimer, the term of this patent is extended or adjusted under 35 U.S.C. 154(b) by 141 days.

(21) Appl. No.: 16/478,225

(22) PCT Filed: Jan. 19, 2018

(86) PCT No.: PCT/EP2018/051323
§ 371 (c)(1),
(2) Date: Jul. 16, 2019

(87) PCT Pub. No.: WO2018/134358
PCT Pub. Date: Jul. 26, 2018

(65) Prior Publication Data
US 2019/0366033 A1    Dec. 5, 2019

(30) Foreign Application Priority Data

Jan. 19, 2017 (EP) ..................... 17152298

(51) Int. Cl.
*A61M 21/02* (2006.01)
*A61B 5/00* (2006.01)
(Continued)

(52) U.S. Cl.
CPC ............. *A61M 21/02* (2013.01); *A61B 5/291* (2021.01); *A61B 5/4094* (2013.01);
(Continued)

(58) Field of Classification Search
CPC ........ A61M 21/00–02; A61M 2230/10; A61B 5/3817; A61B 5/291; A61B 5/375; A61B 5/4812; A61B 5/4836; A61N 1/36036
See application file for complete search history.

(56) References Cited

U.S. PATENT DOCUMENTS 9,579,060 B1 * 2/2017 Lisy ................... A42B 3/0453
2003/0195588 A1  10/2003 Fischell et al.
(Continued)

FOREIGN PATENT DOCUMENTS

EP      2883494 A1   6/2015
WO   2007/047667 A2   4/2007
(Continued)

OTHER PUBLICATIONS

International Search Report dated Jun. 7, 2018 in corresponding International Application No. PCT/EP2018/051323; 4 pages.
(Continued)

*Primary Examiner* — Thaddeus B Cox
(74) *Attorney, Agent, or Firm* — Osha Bergman Watanabe & Burton LLP

(57) ABSTRACT

An in-ear stimulation system including a first device configured to be worn at least partially in a first ear canal of a subject and a second device configured to be worn at least partially in a second ear canal of the subject. Each of the first device and the second device includes:
at least one in-ear active electrode configured to receive a bio-signal and at least one in-ear reference electrode configured to receive a bio-signal;
(Continued)

at least one stimulation device configured for emitting at least one electrical or sensory stimulus; and an electronic system configured to detect at least one bio-signal pattern from the bio-signals measured from the electrodes.

16 Claims, 7 Drawing Sheets

(51) Int. Cl.
    *A61B 5/291*     (2021.01)
    *A61M 21/00*     (2006.01)

(52) U.S. Cl.
    CPC .......... *A61B 5/4812* (2013.01); *A61B 5/6817* (2013.01); *A61M 2021/0022* (2013.01); *A61M 2021/0027* (2013.01); *A61M 2021/0044* (2013.01); *A61M 2205/3553* (2013.01); *A61M 2205/3584* (2013.01); *A61M 2230/10* (2013.01)

(56) References Cited

U.S. PATENT DOCUMENTS

2010/0324440 A1    12/2010    Moore et al.
2015/0164361 A1*    6/2015    Lunner .................. A61B 5/316
                                        600/379

FOREIGN PATENT DOCUMENTS

WO    2011000375 A1    1/2011
WO    2012097872 A1    7/2012
WO    2016102602 A1    6/2016

OTHER PUBLICATIONS

Office Action in counterpart Japanese Patent Application No. 2019-538503 dated Nov. 24, 2021 (9 pages).

* cited by examiner

SYSTEM FOR BILATERAL IN-EAR EEG RECORDING WITH CLOSED-LOOP BINAURAL SENSORY STIMULATION

FIELD OF INVENTION

The present invention pertains to the field of EEG recording medical devices. In particular, the invention relates to an in-ear stimulation system for EEG waves enhancement or cancellation.

BACKGROUND OF INVENTION

Brain is involved in several disorders or diseases that represent real public health issues. They can be related to sleep perturbations, fatigue, neurological or neurobiological disorders such as depression, epilepsy, Parkinson disease, Alzheimer's disease or Attention Deficit/Hyperactivity Disorder (ADHD). There are several ways, such as drugs or medical devices, to alleviate people presenting these disorders/diseases. The latter solutions include devices recording Electroencephalogram (EEG) and providing stimulations at a stage of the brain activity whether during sleep or not.

Depending on the subject's activity, one type of brain waves appears on the recorded EEG. It can be:
- Delta waves (frequency range of 0.5 to 4 Hz): they characterize a deep sleep state without dreams;
- Theta waves (frequency range of 4 to 7 Hz): they characterize deep relaxation state (meditation), somnolence, hypnosis or memorization state;
- Alpha waves (frequency range of 8 to 13 Hz): they characterize mild relaxation state or calm wakefulness state when the eyes are closed;
- Beta waves (frequency range of 14 to 45 Hz): they characterize basic activity and short sleep states with dreams during which the eyes are opened;
- Gamma waves (frequency over 45 Hz): they characterize high brain activity.

There is therefore an alternation between the different waves all day long, for example during the sleep. A night of sleep comprises between 4 and 6 sleep cycles depending on the duration of the night. Each cycle comprises three different phases comprising at least one stage. The sleep phases are:
- the falling sleep which corresponds to stage I. At this stage, Theta waves are recorded on the EEG;
- the slow-wave sleep (SWS) which comprises;
  - the slow-wave light sleep which corresponds to stage II. At this stage, Theta waves are also recorded on the EEG especially sleep spindles and K-complex (frequency range from 10 to 14 Hz);
  - the slow-wave deep sleep which corresponds to stages III and IV. At this stage, Delta waves are recorded on the EEG. They are qualified of slow oscillations (SO) because of their low frequency range and they play an important role in memory enhancement;
- the Rapid Eye Movement (REM) which is similar to the wakefulness state.

Multiple devices implement methods consisting in modifying brain rhythms by applying or emitting stimulation, in particular auditory stimulation, have been developed in recent years.

For instance, WO 2016/102602 describes a device, especially a headband, for monitoring the brain activity and an external stimulation device wherein external electrical, magnetic, sensory or other forms of energy stimuli are applied or emitted at the onset of stage II of a non-REM light sleep cycle. The sensory stimuli may include auditory, olfactory, tactile or other sensory stimuli. The aim of such a device is to allow the enhancement of memory consolidation.

In contrast to the device described in WO 2016/102602, the applicant develops an in-ear binaural stimulation system applying or emitting stimuli directly inside the ear canal of a subject. According to the Applicant, binaural acoustic stimulations are particularly efficient in enhancing specific brain waves.

Furthermore, the applicant demonstrates that an in-ear stimulation system applying or emitting stimuli with a time delay separating stimuli generated from a first stimulation device from stimuli generated from a second stimulation device is even more efficient.

Therefore, the present invention relates to an in-ear stimulation system applying or emitting stimuli directly inside the ear canal.

SUMMARY

The present invention relates to an in-ear binaural stimulation system comprising a first device configured to be worn at least partially in a first ear canal of a subject and a second device configured to be worn at least partially in a second ear canal of the subject; wherein each of the first device and the second device comprise:
- at least one in-ear active electrode configured to receive a bio-signal and at least one in-ear reference electrode configured to receive a bio-signal;
- at least one stimulation device configured for emitting at least one electrical or sensory stimulus; and wherein the in-ear binaural stimulation system further comprises an electronic system configured to detect at least one bio-signal pattern from the bio-signals measured from the electrodes and to trigger, in response to the detection of the at least one bio-signal pattern, a generation of at least one stimulus from the stimulation device of the first device and a generation of at least one stimulus from the stimulation device of the second device.

According to one embodiment, the at least one stimulus generated from the stimulation device of the first device and the at least one stimulus generated from the stimulation device of the second device are temporally separated by an interaural time delay.

According to one embodiment, the at least one in-ear active electrode of the first device is referenced to the at least one in-ear reference electrode of the second device and the at least one in-ear active electrode of the second device is referenced to the at least one in-ear reference electrode of the first device.

According to one embodiment, the interaural time delay between the at least one stimulus generated from the stimulation device of the first device and the at least one stimulus generated from the stimulation device of the second device is ranging from about 1 ms to about 5 s.

According to one embodiment, the electronic system is configured to trigger a generation of a sequence of at least two stimuli from the stimulation device of the first device and a generation of a sequence of at least two stimuli from the stimulation device of the second device.

According to one embodiment, the interaural time delay between a stimulus generated from the stimulation device of the first device and a corresponding stimulus generated from the stimulation device of the second devices varies during a sequence of at least two stimuli.

According to one embodiment, the electronic system is configured so that the first stimulus of a sequence of stimuli is alternatively generated from the stimulation device of the first device and then from the stimulation device of the second device.

According to one embodiment, the stimulation device of the first device and/or the second device is an in-ear stimulation device.

According to one embodiment, the electronic system is configured to detect a bio-signal pattern during a specific stage of the brain rhythm; said stage being preferably during sleep.

According to one embodiment, wherein the electronic system is configured to detect, during sleep, the peak and falling slope of sleep slow waves, and trigger in response to the detection of the peak and falling slope of sleep slow waves, a generation of at least one stimulus from the stimulation device of the first device and from the stimulation device of the second device.

According to one embodiment, the electronic system is configured to trigger a generation of a sequence of at least one stimulus from the stimulation device of the first device and a generation of a sequence of at least one stimulus from the stimulation device of the second device until the end of each sleep cycle.

According to one embodiment, wherein the stimulation device of the first device and/or the second device is an acoustic stimulation device or a vibratory stimulation device.

According to one embodiment, the in-ear binaural stimulation system according to the invention further comprises a visual stimulation device configured to be worn by the subject wherein the electronic system is configured to trigger, in response to the detection of the at least one bio-signal pattern, a generation of at least one visual stimulus from the visual stimulation device.

According to one embodiment, the electronic system comprises an acquisition unit, an amplification unit, a control unit, a processing unit, a memory and a communication unit.

According to one embodiment, the electronic system is embedded in the first device and/or the second device.

According to one embodiment, the bio-signal is generated by a cerebral electrical activity.

According to one embodiment, the at least one in-ear active electrode is configured to receive a local electrical activity generated from at least one area or a combination of areas of the brain including at least one area of the following list: {subiculum, hippocampus, cortex entorhinal}.

Definitions

In the present invention, the following terms have the following meanings:

"About" preceding a figure means plus or less 10% of the value of said figure.

"Acoustic" refers to the sense or organs of hearing, to sound, or to the science of sound.

"Bio-signal" refers to any signal in subjects that can be continually measured and monitored. Bio-signal refers especially to any biological parameter which can be measured by an instrument which converts a physical measure (light, pressure, electricity, radio-signal . . . ) into an analogous signal (in volts) and which is then digitalized. In particular, the bio-signal refers to an electroencephalogram signal.

"Diode" refers to an optoelectronics device emitting light after its supply by an electrical current.

"Electrode" refers to a conductor used to establish electrical contact with a nonmetallic part of a circuit. For instance, EEG electrodes are small metal parts usually made of stainless steel, tin, gold, silver covered with a silver chloride coating; they are placed in the in-ear stimulation device.

"Reference electrode" refers to an electrode whose potential is known. The potential of another electrode can be measured from this latter.

"Active electrode" refers to an electrode which is in charge of the bio-signal acquisition and recording.

"Electroencephalogram" or "EEG" refers to the record of the electrical activity of the brain of a subject, made by electrodes placed in the in-ear stimulation device.

"Faraday cage" refers to an enclosure which is used to protect a device from the electromagnetic environment.

"Interaural time delay" refers herein to the time interval separating one stimulation generated from the first device of the in-ear binaural system from one stimulation generated from the second device of the in-ear binaural system and conversely.

"K-complex" refers to high amplitude, diphasic frontocentral slow waves in the electroencephalogram related to arousal from sleep by a sound; characteristic of sleep stages II, III and IV.

"Subject" refers to a warm-blooded animal, preferably a mammal, more preferably a human.

"Sleep cycle" refers to consecutive stages that comprise: falling asleep, a non-REM sleep state (light state and then deep state) and briefly back to sleep stage II then REM sleep state (during this stage the brain activity is intense, quite close to that of awakening, there are very rapid eye movements).

"Non-REM sleep state" refers to stage I (stage of transition between wakefulness and sleep), stage II (stage of sleep confirmed), stage III, stage IV (stages III and IV are characterized on the EEG by slow and loose waves, hence the name of slow wave sleep).

"Sleep spindle" refers to brain waves that appear during stage II of a non-REM sleep and is the hallmark of an increased brain activity.

"Unit" refers in the field of electronic and computer science, to an element intended to perform a task.

"Acquisition unit" refers to a unit, as defined herein, which receives information from a system.

"Control unit" refers to a unit, as defined herein, which commands and controls the functioning of a system.

"Processing unit" refers to a unit, as defined herein, which is in charge of performing instructions that come from the control unit defined herein.

"Vibratory" refers to an element capable of producing vibrations.

DETAILED DESCRIPTION

The following detailed description will be better understood when read in conjunction with the drawings. For the purpose of illustrating, the system is shown in the preferred embodiments. It should be understood, however that the application is not limited to the precise arrangements, structures, features, embodiments, and aspects shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

This invention relates to an in-ear binaural stimulation system comprising a first in-ear device a second in-ear device and an electronic system.

According to one embodiment, as illustrated in FIG. 2, the first device of the in-ear binaural stimulation system and second in-ear device of the in-ear binaural stimulation system are configured to be worn at respectively right and left ears.

According to one embodiment, as illustrated in FIG. 1, each of the first device of the in-ear binaural stimulation system and second device of the in-ear binaural stimulation system comprises a measurement device and a stimulation device 13, 23.

According to one embodiment, the measurement device of each of the first device of the in-ear binaural stimulation system and second device of the in-ear binaural stimulation system comprises at least one in-ear active electrode 11, 21 which receives a bio-signal and at least one in-ear reference electrode 12, 22 which receives a bio-signal.

According to one embodiment, as illustrated in FIG. 1, each in-ear active electrode 11 of the first device of the in-ear binaural stimulation system is referenced to one in-ear reference electrode 22 of the second in-ear device and each in-ear active electrode 21 of the second device is referenced to one in-ear reference electrode 12 of the first device.

According to one embodiment, the measurement device of each of the first device of the in-ear binaural stimulation system and second device of the in-ear binaural stimulation system comprises one in-ear active electrode 11, 21 which receives a bio-signal and one in-ear reference electrode 12, 22 which receives a bio-signal.

According to one embodiment, the measurement device of each of the first device of the in-ear binaural stimulation system and second device of the in-ear binaural stimulation system comprises two in-ear active electrodes 11, 21 which receive a bio-signal and two in-ear reference electrodes 12, 22 which receives a bio-signal.

According to one embodiment, the measurement device of each of the first device of the in-ear binaural stimulation system and second device of the in-ear binaural stimulation system comprises three in-ear active electrodes 11, 21 which receive a bio-signal and two in-ear reference electrodes 12, 22 which receives a bio-signal.

According to one embodiment, the measurement device of each of the first device of the in-ear binaural stimulation system and second device of the in-ear binaural stimulation system comprises four in-ear active electrodes 11, 21 which receive a bio-signal and two in-ear reference electrodes 12, 22 which receives a bio-signal.

According to one embodiment, the measurement device of each of the first device of the in-ear binaural stimulation system and second device of the in-ear binaural stimulation system comprises five in-ear active electrodes 11, 21 which receive a bio-signal and two in-ear reference electrodes 12, 22 which receives a bio-signal.

According to one embodiment, the number of active electrodes 11, 21 and reference electrodes 12, 22 is equivalent in one device of the in-ear binaural stimulation system.

According to one embodiment, the number of active electrodes 11, 21 and reference electrodes 12, 22 is different in one device of the in-ear binaural stimulation system.

According to one embodiment, the number of active electrodes 11, 21 is superior to the number of reference electrodes 12, 22 in one device of the in-ear binaural stimulation system.

According to one embodiment, each of the first in-ear device active electrodes 11, 21 and second in-ear device active electrodes and first in-ear device reference electrodes 12 and second in-ear device reference electrodes 22 are dry electrodes. In this embodiment, said dry electrodes are made of any non-metallic conductor.

According to one embodiment, said dry electrodes are made of a conductive metal.

According to one embodiment, said dry electrodes are made of metal coated textile.

According to one embodiment, said dry electrodes have an impedance ranging from 10 kiloOhm to 30 kiloOhm, preferably 20 kiloOhm.

According to one embodiment, each of the first device of the in-ear binaural stimulation system and second device of the in-ear binaural stimulation system is configured to be worn at least partially in an ear canal 3 of a subject.

According to one embodiment, each of the first device of the in-ear binaural stimulation system and second device of the in-ear binaural stimulation system is configured to be worn partially in an ear canal 3 of a subject.

According to one embodiment, each of the first device of the in-ear binaural stimulation system and second device of the in-ear binaural stimulation system is configured to be worn entirely in an ear canal 3 of a subject.

According to one embodiment, each of the first device of the in-ear binaural stimulation system and second device of the in-ear binaural stimulation system is made of non-conductive flexible materials.

According to one embodiment, said flexible material is a memory foam.

According to one embodiment, said flexible material is a flexible rubber.

According to one embodiment, the flexible material of the in-ear stimulation system conforms naturally to the shape of a subject ear, enabling good and comfortable contact to the skin inside the ear canal 3.

According to one embodiment, the tight fit between the first or the second device of the in-ear binaural stimulation system and the ear canal 3 ensures that electrodes 11, 21, 12, 21 are held in place thus overcoming common sources of noise like motion or ocular artifacts. This placement of the in-ear binaural stimulation system entails that the latter is only removable by manual action of the subject.

According to one embodiment, the conductive surface of each of the first device of the in-ear binaural stimulation system electrodes 11, 12 and second device of the in-ear binaural stimulation system electrodes 21, 22 has a specific shape enabling a large contact with the ear canal.

According to one embodiment, said conductive surface has a length which is superior to 4 millimeters. In this embodiment, said conductive surface has an orientation of 360°.

In a preferred embodiment, the shape of the conductive surface of each of the first device of the in-ear binaural stimulation system electrodes 11, 12 and second device of the in-ear binaural stimulation system electrodes 21, 22 is an annular shape.

According to one embodiment, the binaural system is from about 20 millimeters to about 30 millimeters high.

According to one embodiment, the binaural system is from about 15 millimeters to about 20 millimeters wide.

According to one embodiment, the binaural system is from about 10 millimeters to about 20 millimeters length.

In a preferred embodiment, the binaural system is 45 millimeters high, 44 millimeters wide and 18 millimeters length.

According to one embodiment, the electronic system is placed inside an ear and directly communicates with each of the first in-ear device of the binaural system and second in-ear device of the binaural system.

According to one embodiment, the electronic system is placed out of an ear and a wired or not wired communication is established between the latter and both of the first and second in-ear devices of the binaural system.

According to one embodiment, the electronic system is configured to detect a bio-signal pattern from said bio-signal measured from the electrodes 11, 12, 21, 22 and to trigger, in response to the detection of said bio-signal pattern, a generation of at least one stimulus from the stimulation device of the first device of the in-ear binaural stimulation system and a generation of at least one stimulus from the stimulation device of the second device of the in-ear binaural stimulation system.

According to the present invention, an interaural time delay separates temporally the at least one stimulus generated from the stimulation device 13 of the first device and the at least one stimulus generated from the stimulation device 23 of the second device.

According to one embodiment, the interaural time delay is ranging from 1 ms to 5 s, preferably about 3 ms.

According to one embodiment, the electronic system is configured to detect a bio-signal pattern from said bio-signal measured from the electrodes 11, 12, 21, 22 and to trigger, in response to the detection of said bio-signal pattern, a generation of at least one sequence of stimuli from the stimulation device of the first device of the in-ear binaural stimulation system and a generation of at least one sequence of stimuli from the stimulation device of the second device of the in-ear binaural stimulation system.

According to one embodiment, the electronic system is configured to detect a bio-signal pattern from said bio-signal measured from the electrodes 11, 12, 21, 22 and to trigger, in response to the detection of said bio-signal pattern, a generation of one to five stimuli from the stimulation device of the first device of the in-ear binaural stimulation system and a generation of one to five stimuli from the stimulation device of the second device of the in-ear binaural stimulation system.

According to one embodiment, the sequence of stimuli from the stimulation device 13 of the first device of the in-ear binaural stimulation system and the sequence of stimuli from the stimulation device 23 of the second device of the in-ear binaural stimulation system occur at the same time.

According to one embodiment, as illustrated in FIG. 3, the sequence of stimuli from the stimulation device 13 of the first device of the in-ear binaural stimulation system does not occur at the same time as the sequence of stimuli from the stimulation device 23 of the second in-ear device of the in-ear binaural stimulation system.

According to one embodiment, the interaural time delay between the at least one sequence of stimuli generated from the stimulation device 13 of the first device of the in-ear binaural stimulation system and the at least one sequence of stimuli generated from the stimulation device 23 of the second device of the in-ear binaural stimulation system is ranging from about 1 ms to about 5 s.

In a preferred embodiment, the interaural time delay between the at least one sequence of stimuli generated from the stimulation device 13 of the first device of the in-ear binaural stimulation system and the at least one sequence of stimuli generated from the stimulation device 23 of the second device of the in-ear binaural stimulation system is about 3 ms.

According to one embodiment, the interaural time delay between a stimulus generated from the first in-ear stimulation device 13 and a corresponding stimulus generated from the second in-ear device stimulation device 23 varies during a sequence of stimuli.

According to one embodiment, the electronic system is configured so that the first stimulus of a sequence of stimuli is alternatively generated from the stimulation device 13 of the first device and then from the stimulation device 23 of the second device.

According to one embodiment, the electronic system is configured to detect a bio-signal pattern during a specific stage of the brain rhythm either during sleep or not.

According to one embodiment, the electronic system is configured to detect, during sleep, the peak and falling slope of slow oscillations, and trigger in response to the detection of the peak and falling slope of slow oscillations, a generation of at least one stimulus from the stimulation device 13 of the first device and at least one stimulus from the stimulation device 23 of the second device.

According to one embodiment, the electronic system is configured to trigger a generation of at least one stimulus from the first in-ear device stimulation device 13 and a generation of at least one stimulus from the second stimulation device 23 until the end of each sleep cycle.

According to one embodiment, as illustrated in FIG. 5, the electronic system comprises an acquisition and amplification unit, a control unit, a processing unit, a communication unit and a memory.

According to one embodiment, the control unit order tasks to the other units.

According to one embodiment, the acquisition and amplification unit receives, from the control unit, the instruction of acquiring and amplifying a bio-signal.

According to one embodiment, the acquisition and amplification unit is linked to the electrodes 11, 12, 21, 22 of the first and second devices of the in-ear binaural stimulation system; said acquisition and amplification unit receives a bio-signal from the first in-ear device of the binaural system electrodes 11, 12 and the second in-ear device of the binaural system electrodes 21, 22 in a wireless way or not.

According to one embodiment, the processing unit receives, from the control unit, the instructions of triggering acoustic stimulations inside an ear, after the detection of a specific stage of the brain wave by the acquisition and amplification unit.

According to one embodiment, the memory is configured to store data provided after the processing step by the processing unit.

According to one embodiment, the electronic system further comprises a remote system.

According to one embodiment, the communication unit receives from the control unit the instruction of sending the stored data to said remote system.

According to one embodiment, the communication unit is linked wirelessly or not with the remote system.

According to one embodiment, the link with the communication unit and the remote system is made through a Bluetooth link. In a preferred embodiment, the Bluetooth link is of 2.4 GHz.

According to one embodiment, the remote system is a computer system, for example a mobile phone or a laptop or any other computer system.

According to one embodiment, the electronic system is embedded in the first device of the binaural system and/or the second device of the binaural system.

According to one embodiment, the stimulation device 13, 23 of each of the first in-ear device of the binaural system and the second in-ear device of the binaural system allows the emission of sequences of electrical sensory stimuli.

According to one embodiment, the stimulation device 13, 23 of the first device of the binaural system and/or the second device of the binaural system is an acoustic stimulation device or a vibratory stimulation device.

According to one embodiment, said acoustic stimulation device or said vibratory stimulation device emits at least one acoustic stimulus or at least one vibratory stimulus in the ear canal.

According to one embodiment, said acoustic stimulation device or said vibratory stimulation device emits a sequence of acoustic stimuli or a sequence of vibratory stimuli in the ear canal 3.

According to one embodiment, the sequences of acoustic simulations comprise two consecutive acoustic stimulations at targeted phases of the bio-signal.

According to one embodiment, the acoustic stimulation device or a vibratory stimulation device triggers sequences of acoustic stimulation or vibratory stimulation directly in the ear.

According to one embodiment, the stimulations of the stimulation device 13, 23 are made at variable frequencies and/or intensities.

According to one embodiment, the sound timing, duration, frequency, intensity and interaural delays of the stimulation device 13, 23 are predefined.

According to one embodiment, the sound duration is predefined for values from 0.05 seconds to 5400 seconds.

According to one embodiment, the sound frequency is predefined for values from 20 Hz to 20 kHz. According to one embodiment, the sound intensity is predefined for values from 40 dB to 80 dB.

According to one embodiment, the sound interaural time delays are predefined for values from 0 seconds to 0.5 seconds, preferably 0.1 second. In a preferred embodiment, the sound duration is predefined at 0.05 seconds.

In a preferred embodiment, the sound frequency is predefined as a mixed pink noise containing all the range of frequencies.

In a preferred embodiment, the sound intensity is predefined at 60 dB.

According to embodiment, the stimulation devices 13, 23 are embedded sensory stimulators.

According to embodiment, the stimulation devices 13, 23 are embedded microphones.

According to one embodiment, the in-ear binaural stimulation system further comprises a visual stimulation device.

According to one embodiment, the visual stimulation device is configured to be worn by the subject during the sleep or not. In this embodiment, the subject wear the visual stimulation device in front of the eyes.

According to one embodiment, the visual stimulation device comprises a pair of glasses or a textile mask wherein a light system emitting visible light is embedded.

According to one embodiment, the visual stimulation system comprises a processing unit under the control of the control unit of the electronic system.

According to one embodiment, the processing unit of the visual stimulation device receives from the control unit of the electronic system, the instruction of generating a sequence of at least one visual stimulus in response to the detection of a bio-signal pattern measured from the electrodes 11, 12, 21, 22 of the in-ear devices.

According to one embodiment, the processing unit of the visual stimulation device receives from the control unit of the electronic system, the instruction of generating a sequence of one to five visual stimuli in response to the detection of a bio-signal pattern measured from the electrodes 11, 12, 21, 22 of the in-ear devices.

According to one embodiment, the stimulations from the visual stimulation system are made at variable frequencies and/or intensities.

According to one embodiment, the light system comprises light emitting diodes having various colors.

According to one embodiment, the visual stimulus duration, frequency, intensity of the visual stimulation device is predefined.

According to one embodiment, the visual stimulus duration is predefined for values from 0.05 seconds to 5400 seconds.

According to one embodiment, the visual stimulus frequency is predefined for values from 0.5 Hz to 20 Hz.

According to one embodiment, the visual stimulus intensity is predefined for values from 0.3 $cd/m^2$ to 1.5 $cd/m^2$.

According to one embodiment, the bio-signal is any signal in subjects that can be continually measured and monitored.

In a preferred embodiment, bio-signal is any biological parameter which can be measured by an instrument which converts a physical measure (light, pressure, electricity, radio-signal . . . ) into an analogous signal (in volts) and which is then digitalized.

According to one embodiment, the in-ear binaural system is configured to monitor several physiological activities.

According to one embodiment, the in-ear binaural system is configured to monitor cardiac rhythm, temperature, O2 saturation, electrodermal activity or motions.

In a preferred embodiment, the bio-signal herein describes an electroencephalogram signal which is a biological signal which comes from the electrical activity of the brain of a subject recorded by electrodes 11, 12, 21, 22 placed in the in-ear stimulation device.

According to one embodiment, as illustrated in FIG. 2, each of the first device of the in-ear binaural system and second in-ear binaural system comprises a conductive part 15 outside of the ear canal of the subject configured to provide electromagnetic shielding and create by this way a Faraday cage. In this embodiment, the Faraday cage of each of the first device of the binaural in-ear system and second device of the in-ear binaural system isolates the in-ear electrodes from the electromagnetic environment.

According to one embodiment, the in-ear binaural system is powered by a rechargeable battery.

According to one embodiment, the invention enables an auditory and/or visual modulation of sleep slow waves and could benefit people presenting sleep perturbations and/or altered memory performance, such as depression, Parkinson or Alzheimer's disease.

According to one embodiment, the invention enables epilepsy seizures detection.

According to one embodiment, EEG-triggered bilateral auditory stimulations can be used to block epileptic seizures at onset.

According to one embodiment, visual stimulations can be used to help a subject to get relaxed.

The present invention also relates to a method of use of the system which consists in initiating and enhancing slow oscillations during a sleep cycle in synchrony with a brain's own rhythm.

Other applications of the present invention may include neurofeedback, Brain Computer Interface, fatigue monitoring, assessment/monitoring of the effect and efficacy of treatment/rehabilitation, estimation of auditory attention or hypoglycemia.

According to one embodiment, the invention enables detection of mesial epileptic discharges.

According to one embodiment, the invention enables differentiation between different epileptic syndromes such as for example between focal epilepsy and primary generalized epilepsy.

According to one embodiment, the invention enables detection of seizure-prone states (e.g. preictal period) and monitoring of pharmacological response in epileptic individuals.

According to one embodiment, the invention enables the correction of lateralization and lobar and/or sub-lobar localization of the epileptogenic zone in focal epilepsy.

According to one embodiment, the invention enables detection of deep electrophysiological abnormalities associated with other neurological disorders such as of example neurodegenerative and neuroinflammatory disorders.

According to one embodiment, the at least one in-ear active electrode (11, 21) is arranged to receive a local electrical activity generated from at least one area or a combination of areas of the brain including at least one area of the following list: subiculum, hippocampus, cortex entorhinal.

According to one embodiment, the at least one in-ear active electrode (11, 21) is arranged to be maintained inside an ear of a subject in order to acquire local electrical activities generated from at least one area of the temporal lobe.

According to one embodiment, the at least one in-ear active electrode (11, 21) is arranged to be maintained inside an ear of a subject in order to acquire local electrical activities generated from a combination of areas of the temporal lobe of the brain including at least one area of the following list: subiculum, hippocampus, cortex entorhinal.

While various embodiments have been described and illustrated, the detailed description is not to be construed as being limited hereto. Various modifications can be made to the embodiments by those skilled in the art without departing from the true spirit and scope of the disclosure as defined by the claims.

REFERENCES

I—Inion;
N—Nasion;
11—Active electrode of the first device of the in-ear binaural stimulation system;
12—Reference electrode of the first device of the in-ear binaural stimulation system;
13—Stimulation device of the first device of the in-ear binaural stimulation system;
14—Memory foam of the first device of the in-ear binaural stimulation system;
15—Conductive part of the first device of the in-ear binaural stimulation system;
21—Active electrode of the second device of the in-ear binaural stimulation system;
22—Reference electrode of the second device of the in-ear binaural stimulation system;
23—Stimulation device of the second device of the in-ear binaural stimulation system;
3—Ear canal;
4—Ear drum;
5—Outer ear;
63—Point where the SO wave cross the abscissa axis (Zero-crossing);
641—Time between the last positive maximal of one period of a SO wave (P) and the last negative minimal of one period of a SO wave (N) for the corresponding negative hemicycle (SO Halfwave-PN) of a first SO wave;
642—Time between the last P and the last N for the corresponding negative hemicycle (SO Halfwave-PN) of a second SO wave;
643—Time between the last P and the last N for the corresponding negative hemicycle (SO Halfwave-PN) of a third SO wave;
651—Time between the zero-crossings for the corresponding negative hemicycle (SO Halfwave-CC) of a first SO wave;
652—Time between the zero-crossings for the corresponding negative hemicycle (SO Halfwave-CC) of a second SO wave;
653—Time between the zero-crossings for the corresponding negative hemicycle (SO Halfwave-CC) of a third SO wave;
661—Phase for stimulation of a first SO wave;
662—Phase for stimulation of a second SO wave;
663—Phase for stimulation of a third SO wave;
671—Mean of the last non-simulated phase for stimulation of a first SO wave;

672—Mean of the last non-simulated phase for stimulation of a second SO wave;
673—Mean of the last non-simulated phase for stimulation of a third SO wave.

EXAMPLES

The present invention is further illustrated by the following examples.

Example 1

Figure 6A:
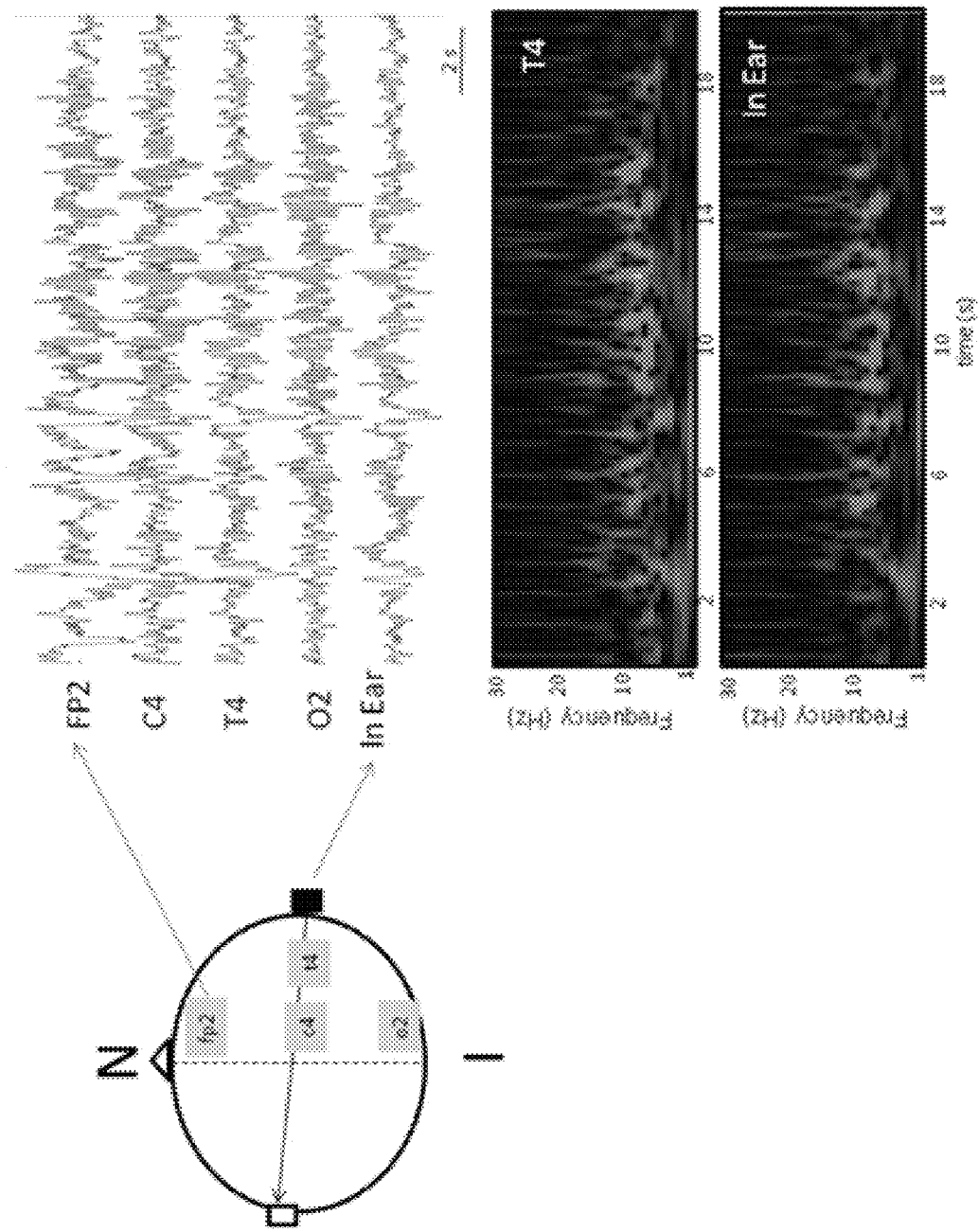
FIG. 6A illustrates a comparison between a standard EEG obtained by EEG recording directly on the scalp and in-ear EEG recording, during resting alpha oscillations.
Figure 6B:
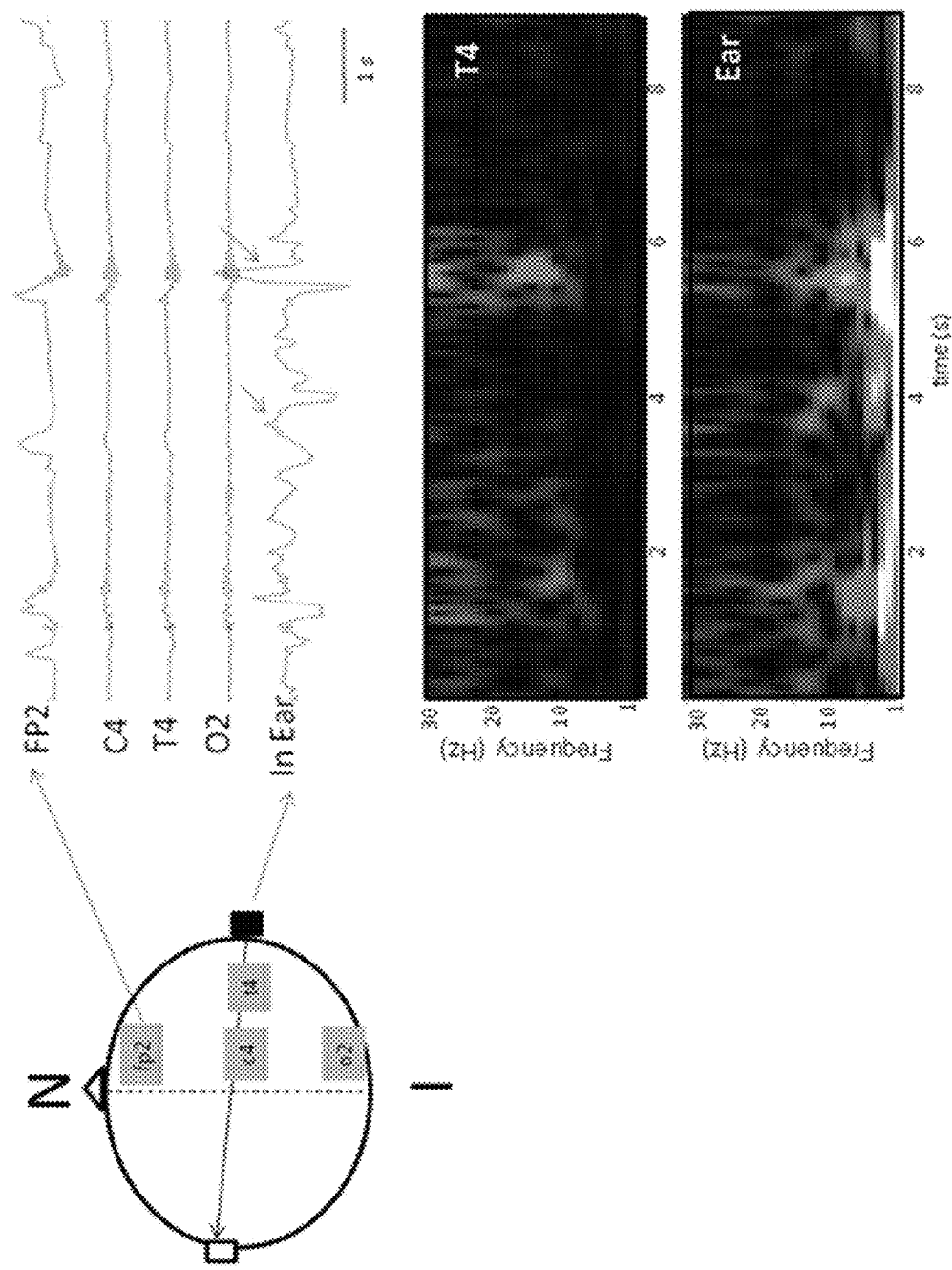
FIG. 6B illustrates a comparison between a standard EEG obtained by EEG recording directly on the scalp and in-ear EEG recording, during K-complex/spindles oscillations.

Comparison Between a Standard EEG Obtained by EEG Recording Directly on the Scalp and Ear-EEG Recordings, During Resting Alpha Oscillations as Illustrated in FIG. 6A and Sleep K-Complexes and Spindles Oscillations as Illustrated in FIG. 6B Method The first tests have been made on three subjects. The in-ear electrodes were silver electrodes or silver-coated electrodes and were tested simultaneously with scalp electrodes using a commercial amplifier from Micromed SAS, in order to enable a fair comparison.

Result

The EEG signals recorded inside the ear canal closely match those obtained for scalp-EEG electrodes (with a contralateral mastoid reference M1-M2) at the temporal locations (T3-T4). A good correspondence within the time-frequency domain was seen during resting alpha oscillations (a wave underpinning eye-closed resting or fatigue, 8-12 Hz), sleep K-complexes and sleep spindles (10-14 Hz, sleep stage II).

Conclusion

In-ear EEG is able to describe the dynamics that have been uncovered using conventional scalp EEG at the temporal region, where the primary auditory cortex is located.

Example 2

Figure 7:
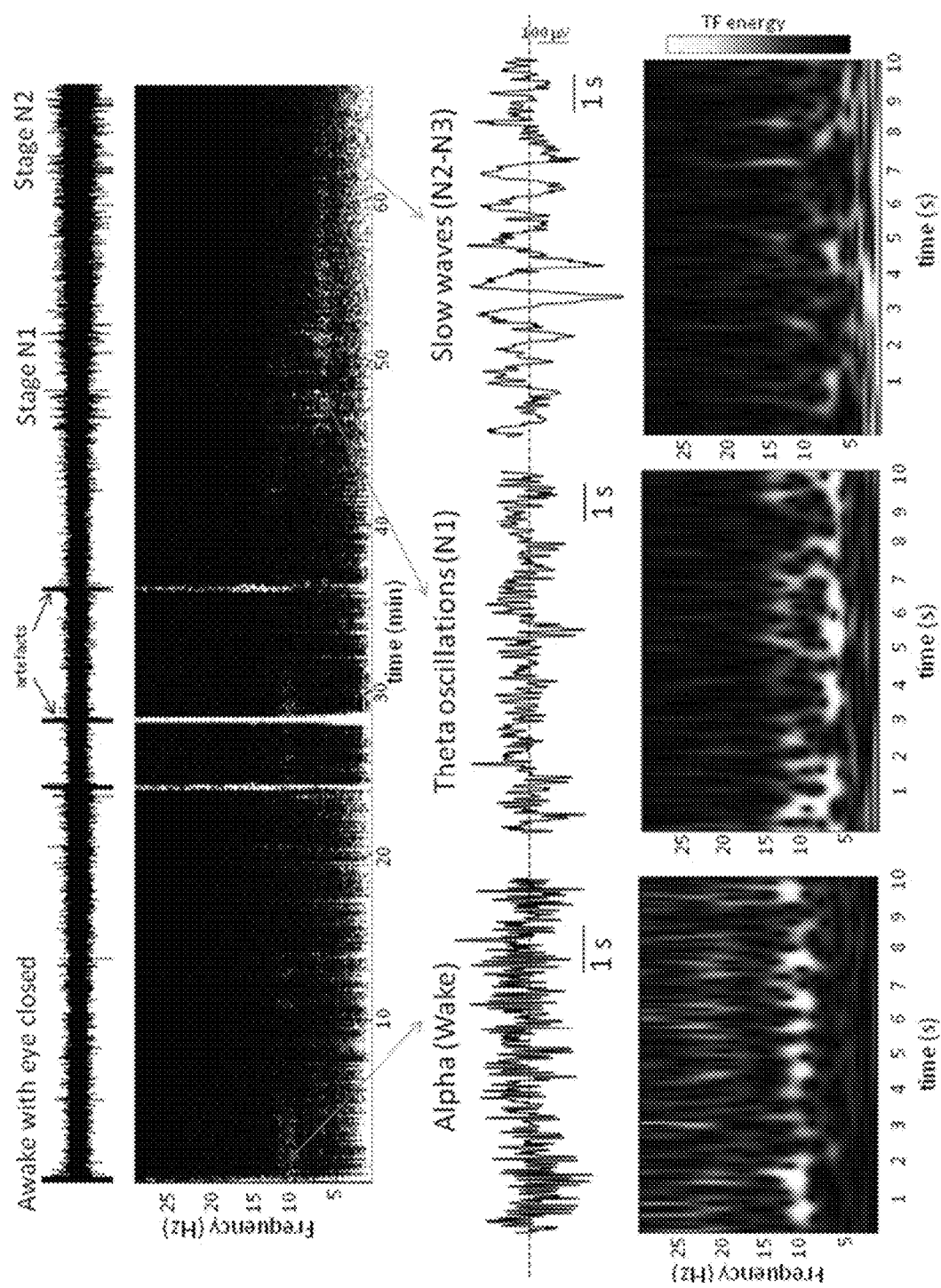
FIG. 7 is an in-ear EEG recording during sleep using the embedded electronic system of the present invention.

Prototype and Tests for Continuous In-Ear EEG Monitoring as Illustrate in FIG. 7

Materials and Methods

Material a microcontroller ATXMEGA128A comprising the control unit, the processing unit and the memory;
a ADS1298 comprising the acquisition unit and the amplification unit;
a Bluetooth HC-05 module comprising the communication module.

Methods

The microcontroller orders the ADS1298, which characteristics are 8 channels, 256 SPS and 24 bits, to acquire and amplify the signals via a SPI (Serial Peripheral Interface) communication. The latter is sent back to the microcontroller ATXMEGA128A which 128 Kb memory allows data storage and communicates the stored data to the Bluetooth HC-05. The communication between the ADS1298 and the Bluetooth HC-05 is an USART (Universal Synchronous/Asynchronous Receiver Transmitter) communication. The Bluetooth HC-05 allows by this way a communication with the remote system.

Results

An implementation of the device (involving both electronic system and first and second devices of in-ear binaural stimulation system) was tested on a subject over several consecutive hours including one night sleep. The measurements were transmitted through conductive leads to the electronic system and then stored to a laptop via a Bluetooth link.

In-ear EEG signals are of good quality with an acceptable number of artifacts and low noise interferences. Sleep standard grapho-elements such as K-complexes, spindles and slow waves can be well identified. Further validation of the sleep patterns was confirmed from spectral analysis where overlapping power distributions with EEG scalp waves has been found.

Example 3

Figure 1:
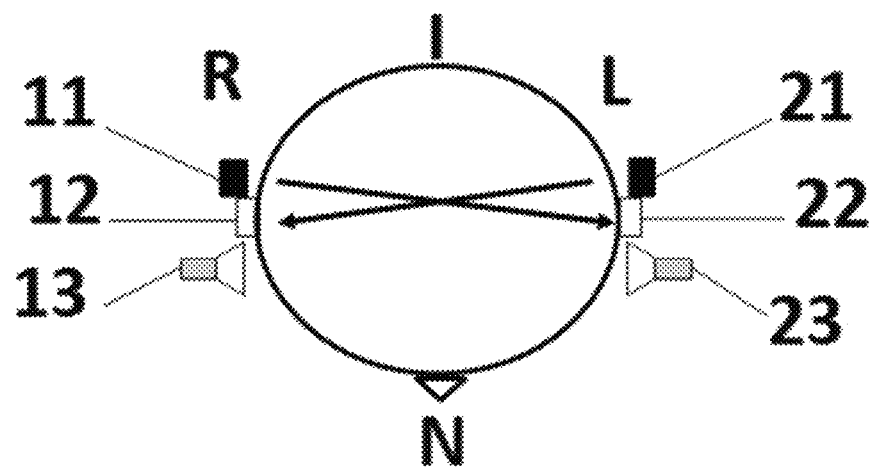
FIG. 1 illustrates the position of the first and second device of the in-ear binaural system. The first device active electrode is referenced to the second device reference electrode; and the second device active electrode is referenced to the first device reference electrode.
Figure 2:
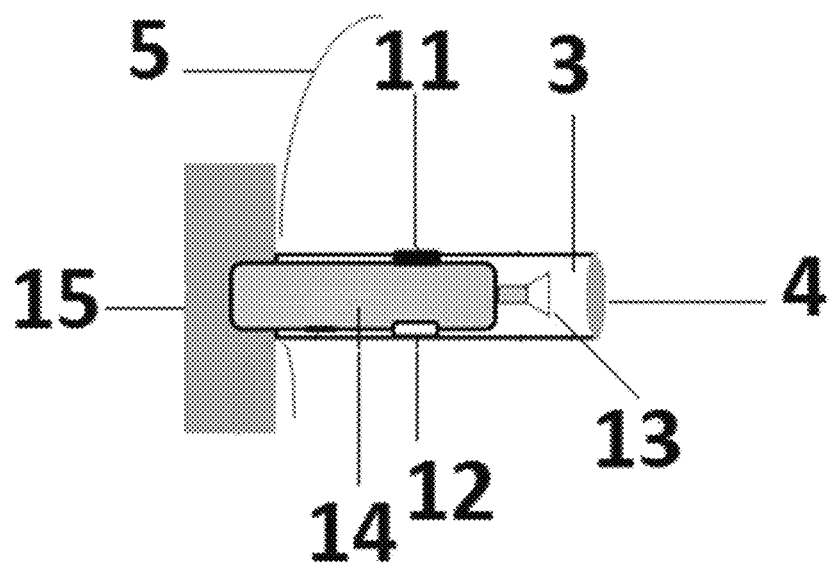
FIG. 2 is a cross-sectional view of the first device of the in-ear binaural system worn at an ear.
Figure 3:
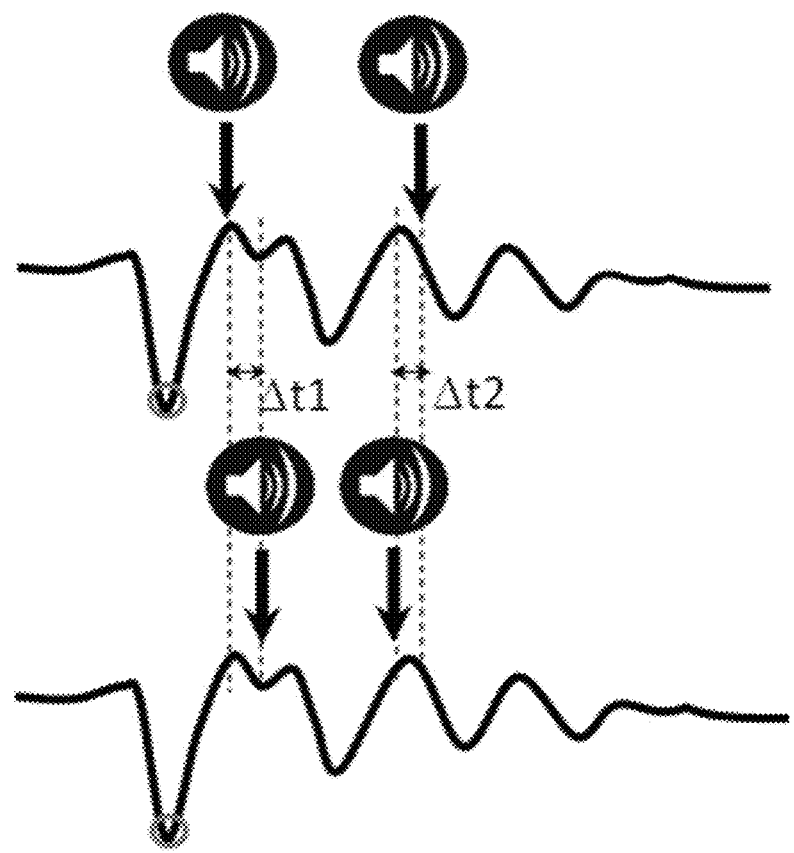
FIG. 3 illustrates the interaural time delay separating a stimulus generated from the stimulation device of the first device (A) of the in-ear binaural stimulation system from a stimulus generated from the stimulation device of the second device (B) of the in-ear binaural stimulation system.
Figure 4:
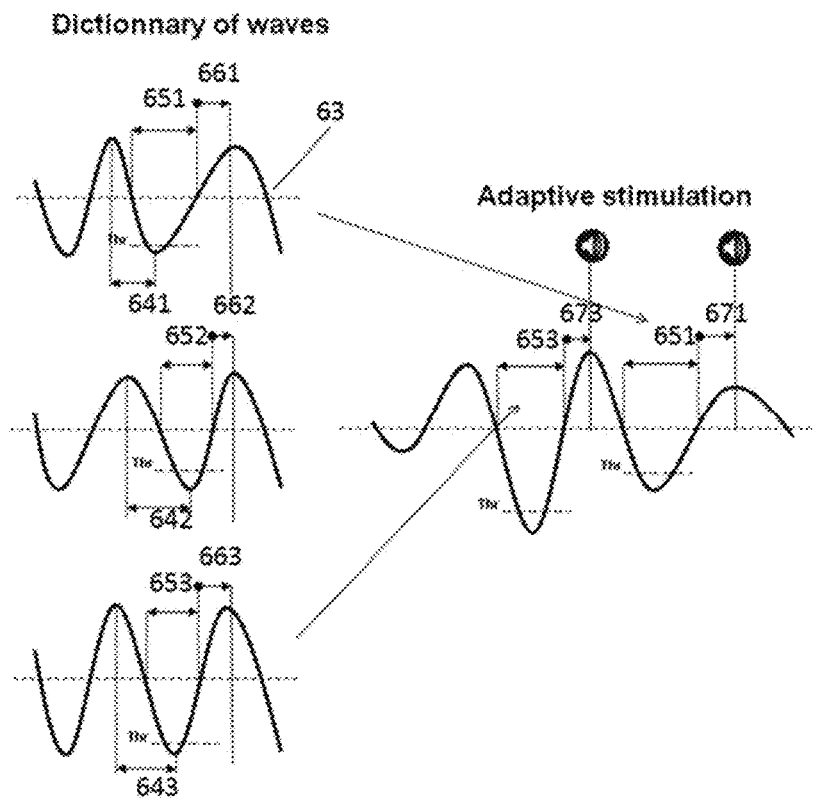
FIG. 4 illustrates the online detection of slow oscillations and subsequent stimulations.
Figure 5:
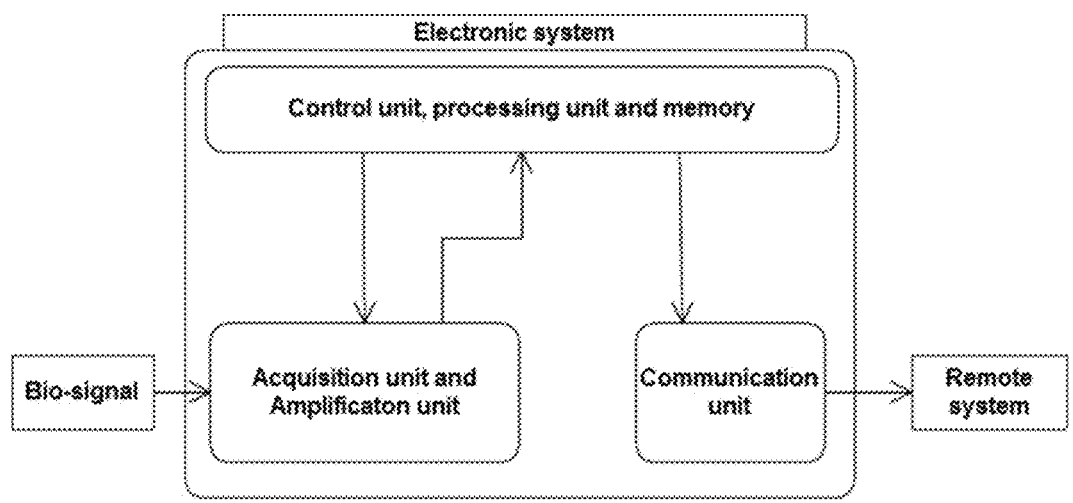
FIG. 5 is a diagram illustrating the in-ear binaural stimulation system.

Online Detection of SO and Stimulations Performing as Illustrated in FIG. 4

Method

Slow oscillations are detected as follows:
The signal is on-line pre-processed by applying a low-pass filter in the SO frequency band (0.5-3 Hz). The positive maximal P and the negative minimal N points of each hemicycle are constantly stored if their absolute value is greater than a marginal magnitude. Each time that the N magnitude of the filtered signal surpass a negative threshold, the system checks the time between the last P and the last N (SO-Halfwave-PN 641, 642, 643) and the time between the zero-crossings 63 for the corresponding negative hemicycle (SO-Halfwave-CC 651, 652, 653). If the times for SO-Halfwave-PN 641, 642, 643 and SO-Halfwave-CC 651, 652, 653 are within the interval of a half of the period of the SWS frequency band, then the current oscillation is considered as a SO. For every accepted SO, the system keeps tracking the time between the ascending zero-crossing 63 point and the preferred phase to be stimulated 661, 662, 663. This duration value 661, 662, 663 is stored and categorized depending on the last SO-Halfwave-CC time 651, 652, 653.

Stimulations are made as follow:
When stimulation is set, and for the wave to be considered as a SO, the times for SO-Halfwave-PN 641, 642, 643 and SO-Halfwave-CC 651, 652, 653 must be within the interval of a half of the period of the SO frequency band, and the N magnitude of the filtered signal must surpass the negative threshold. Once the SO is detected, the SO is categorized depending on the last SO-Halfwave-CC 651, 652, 653 time, and a stimulation is sent a time after the ascending zero-crossing 63 point afterwards N. This time corresponds to the mean of the last non-stimulated 671, 672, 673 phase for stimulation of a given SO wave 661, 662, 663 of the selected category. After stimulation, the magnitude of the negative threshold is reduced half of the value for the next detection. The amplitude threshold is reset once a time is achieved where no SO are detected, or when a minimal threshold magnitude is reached.

Example 4

Comparison Between a Standard EEG Obtained by EEG Recording Directly on the Scalp and Ear-EEG Recordings During Subjects' Sleep as Illustrated in FIG. 8

Method

Figure 8A:
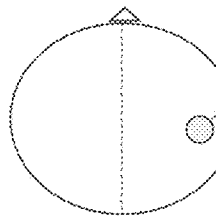
FIG. 8a is a schematic representation of the position of the in-ear EEG in the ear of subject and scalp EEG on the head of a subject.

The preliminary tests have been made on three subjects for which five sleep recordings have been acquired. The in-ear electrodes were silver electrodes or silver-coated electrodes and were tested simultaneously with scalp electrodes at the temporal locations (T3 or T4) using a commercial amplifier from Micromed SAS, in order to enable a fair comparison (FIG. 8a).

Slow oscillations are detected as follows:

For both scalp and in-ear signals, an automatic detection of slow waves (SO) was performed separately for the in-ear electrode and the scalp electrode and for a whole recorded night. Only events detected during episodes marked as non-rapid eye movement sleep (NREM) were used for the analysis.

SO waves detection was achieved similarly to already published procedures (Clemens et al., 2007, "Temporal coupling of parahippocampal ripples, sleep spindles and slow oscillations in humans", *Brain* 130, 2868-78).

Specially, raw data were filtered in the 0.3-3 Hz frequency band through a Chebyshev filter with zero-phase correction. Signal deflections with negative peak inferior or equal to −80 µV (represented by the double-headed arrow referenced as B in FIG. 8c) within a zero-crossing interval between 300 ms and 1 second (represented by the double-headed arrow referenced as A in FIG. 8c) and a subsequent peak to peak amplitude superior or equal to −140 µV (represented by the double-headed arrow referenced as C in FIG. 8c) were considered as SO waves.

Results

In 37% of the cases (illustrative example of a subject in FIG. 8c), we found that the inter-ear referenced in-ear EEG signals of SO waves closely match those obtained for scalp-EEG electrodes.

Figure 8B:
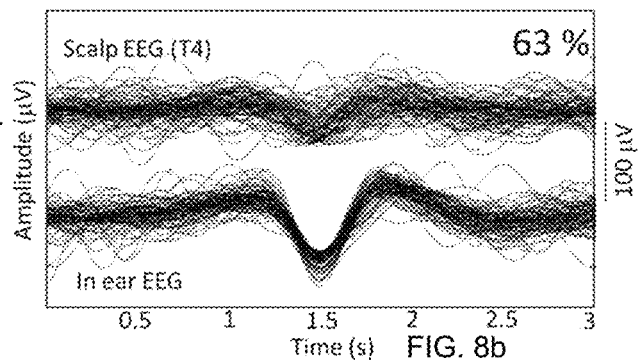
FIGS. 8b and 8c are in-ear EEG and scalp EEG recording of SO slow wave.
Figure 8C:
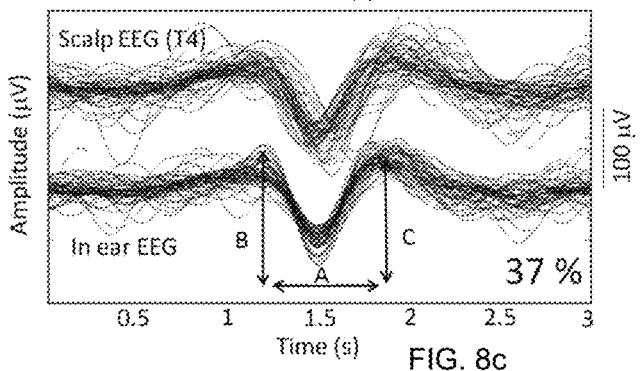

Nevertheless, in most of the cases (63%) SO waves could be identified in in-ear electrodes without significant activations of the scalp electrodes (FIG. 8b).

CONCLUSION

These results suggest that in-ear sensors can provide novel information that may not be overtly seen in the surface recording. Moreover, in-ear EEG may contain additional physiological properties such as deep limbic physiological activations associated with memory consolidation during sleep (Clemens et al., 2007, "Temporal coupling of parahippocampal ripples, sleep spindles and slow oscillations in humans", *Brain* 130, 2868-78).

The invention claimed is:

1. An in-ear binaural stimulation system comprising a first device configured to be worn at least partially in a first ear canal of a subject and a second device configured to be worn at least partially in a second ear canal of the subject; wherein each of the first device and the second device comprises:
   at least one in-ear active electrode configured to receive a bio-signal and at least one in-ear reference electrode configured to receive a bio-signal;
   at least one stimulation device configured for emitting at least one electrical or sensory stimulus; and wherein
   the in-ear binaural stimulation system further comprises an electronic system configured
   to detect at least one bio-signal pattern from the bio-signals received from said at least one in-ear active electrode and said at least one in-ear reference electrode of the first device and said at least one in-ear active electrode and said at least one in-ear reference electrode of the second device and
   to trigger, in response to the detection of the at least one bio-signal pattern, a generation of at least one stimulus from the at least one stimulation device of the first device and a generation of at least one stimulus from the at least one stimulation device of the second device, wherein
   the at least one in-ear active electrode of the first device is referenced to the at least one in-ear reference electrode of the second device and the at least one in-ear active electrode of the second device is referenced to the at least one in-ear reference electrode of the first device.

2. The in-ear binaural stimulation system according to claim 1, wherein the at least one stimulus generated from the at least one stimulation device of the first device and the at least one stimulus generated from the at least one stimulation device of the second device are temporally separated by an interaural time delay.

3. The in-ear binaural stimulation system according to claim 2, wherein the interaural time delay between the at least one stimulus generated from the at least one stimulation device of the first device and the at least one stimulus generated from the at least one stimulation device of the second device ranges from about 1 ms to about 5 s.

4. The in-ear binaural stimulation system according to claim 2, wherein the electronic system is configured to trigger a generation of a sequence of at least two stimuli from the at least one stimulation device of the first device and a generation of a sequence of at least two stimuli from the at least one stimulation device of the second device.

5. The in-ear binaural stimulation system according to claim 4, wherein the interaural time delay between a stimulus generated from the at least one stimulation device of the first device and a corresponding stimulus generated from the at least one stimulation device of the second devices varies during a sequence of at least two stimuli.

6. The in-ear binaural stimulation system according to claim 4, wherein the electronic system is configured so that the first stimulus of a sequence of stimuli is alternatively generated from the at least one stimulation device of the first device and then from the at least one stimulation device of the second device.

7. The in-ear stimulation system according to claim 1, wherein the at least one stimulation device of the first device and/or the second device is an in-ear stimulation device.

8. The in-ear binaural stimulation system according to claim 1, wherein the electronic system is configured to detect said at least one bio-signal pattern during a specific stage of a brain rhythm.

9. The in-ear binaural stimulation system according to claim 8, wherein the electronic system is configured to trigger a generation of a sequence of at least one stimulus from the at least one stimulation device of the first device and a generation of a sequence of at least one stimulus from the at least one stimulation device of the second device until the end of a sleep cycle.

10. The in-ear binaural stimulation system according to claim 1, wherein the electronic system is configured to detect, during sleep, the peak and falling slope of sleep slow waves, and trigger in response to the detection of the peak and falling slope of sleep slow waves, a generation of at least one stimulus from the at least one stimulation device of the first device and from the at least one stimulation device of the second device.

11. The in-ear binaural stimulation system according to claim 1, wherein the at least one stimulation device of the first device and/or the second device is an acoustic stimulation device or a vibratory stimulation device.

12. The in-ear binaural stimulation system according to claim 1, further comprising a visual stimulation device configured to be worn by the subject wherein the electronic system is configured to trigger, in response to the detection of the at least one bio-signal pattern, a generation of at least one visual stimulus from the visual stimulation device.

13. The in-ear binaural stimulation system according to claim 1, wherein the electronic system comprises an acquisition unit, an amplification unit, a control unit, a processing unit, a memory and a communication unit.

14. The in-ear binaural stimulation system according to claim 1, wherein the electronic system is embedded in the first device and/or the second device.

15. The in-ear binaural stimulation system according to claim 1, wherein the bio-signals received from said at least one in-ear active electrode and said at least one in-ear reference electrode of the first device and said at least one in-ear active electrode and said at least one in-ear reference electrode of the second device are generated by a cerebral electrical activity.

16. The in-ear binaural stimulation system according to claim 1, wherein the at least one in-ear active electrode of the first device and the at least one in-ear active electrode of the second device are configured to receive a local electrical activity generated from at least one area or a combination of areas of the brain of the subject including at least one area of the following list: subiculum, hippocampus, entorhinal cortex.

* * * * *